United States Patent
Mitra et al.

(10) Patent No.: US 9,116,141 B2
(45) Date of Patent: Aug. 25, 2015

(54) MICROTRAP ASSEMBLY FOR GREENHOUSE GAS AND AIR POLLUTION MONITORING

(75) Inventors: Somenath Mitra, Bridgewater, NJ (US); Chutarat Saridara, Bangkok (TH)

(73) Assignee: New Jersey Institute of Technology, Newark, NJ (US)

(*) Notice: Subject to any disclaimer, the term of this patent is extended or adjusted under 35 U.S.C. 154(b) by 0 days.

(21) Appl. No.: 13/085,590

(22) Filed: Apr. 13, 2011

(65) Prior Publication Data

US 2011/0271838 A1  Nov. 10, 2011

Related U.S. Application Data

(60) Provisional application No. 61/323,864, filed on Apr. 13, 2010.

(51) Int. Cl.

| | |
|---|---|
| *B01D 53/02* | (2006.01) |
| *G01N 30/08* | (2006.01) |
| *G01N 1/40* | (2006.01) |
| *G01N 30/60* | (2006.01) |
| *B01D 53/04* | (2006.01) |
| *B01D 53/30* | (2006.01) |
| *B01D 53/70* | (2006.01) |

(Continued)

(52) U.S. Cl.
CPC ............ *G01N 30/08* (2013.01); *B01D 53/0407* (2013.01); *B01D 53/30* (2013.01); *B01D 53/70* (2013.01); *B01D 53/72* (2013.01); *B82Y 30/00* (2013.01); *G01N 1/405* (2013.01); *G01N 30/6095* (2013.01); *B01D 2253/102* (2013.01); *B01D 2253/304* (2013.01); *B01D 2253/342* (2013.01); *B01D 2257/2064* (2013.01); *B01D 2257/2066* (2013.01); *B01D 2257/708* (2013.01); *B01D 2257/7025* (2013.01); *G01N 2030/062* (2013.01); *G01N 2030/085* (2013.01); *Y02C 20/20* (2013.01)

(58) Field of Classification Search
CPC ......... G01N 1/40; G01N 1/405; G01N 30/08; G01N 30/6095; G01N 2030/062; G01N 2030/085; B01D 53/0407; B01D 53/0423; B01D 2253/102; B01D 2253/304
USPC ........ 96/101, 102, 103, 104, 105, 108; 95/82, 95/87, 88, 89; 73/23.35, 23.39, 23.41; 977/742, 752
See application file for complete search history.

(56) References Cited

U.S. PATENT DOCUMENTS

| | | |
|---|---|---|
| 5,435,169 A | 7/1995 | Mitra |
| 7,147,695 B2 | 12/2006 | Mitra |

(Continued)

OTHER PUBLICATIONS

D.J. Butcher, The real-time analysis of gases by direct sampling-mass spectrometry: elemental and molecular applications, Microchemical Journal, 66 (2000) 55-72.

(Continued)

*Primary Examiner* — Robert Clemente
(74) *Attorney, Agent, or Firm* — Timothy X. Gibson; Gibson & Dernier LLP

(57) ABSTRACT

A microtrap assembly includes a carbon nanotube sorbent. The microtrap assembly may be employed as a preconcentrator operable to deliver a sample to an analytical device to measure the concentrations of greenhouse gases. A system includes a microtrap having a carbon nanotube sorbent for measuring the concentrations of greenhouse gases in a sample.

23 Claims, 7 Drawing Sheets

(51) Int. Cl.
*B01D 53/72* (2006.01)
*B82Y 30/00* (2011.01)
*G01N 30/06* (2006.01)

(56) References Cited

U.S. PATENT DOCUMENTS

| | | | | |
|---|---|---|---|---|
| 7,608,818 | B2 * | 10/2009 | Miller et al. | 250/288 |
| 7,615,189 | B2 * | 11/2009 | Aslam et al. | 422/69 |
| 8,123,834 | B2 * | 2/2012 | Masel et al. | 95/90 |
| 8,127,595 | B2 * | 3/2012 | Finlay et al. | 73/31.07 |
| 8,132,443 | B2 * | 3/2012 | McGill et al. | 73/23.39 |
| 2004/0224425 | A1 * | 11/2004 | Gjerde et al. | 436/518 |
| 2008/0175785 | A1 * | 7/2008 | Mitra et al. | 423/445 B |

OTHER PUBLICATIONS

E Diaz, S. Ordonez, A. Vega, J., Adsorption of volatile organic compounds onto carbon nanotubes, carbon nanofibers, and high-surface-area graphites; Journal of Colloid and Interface Science 305 (2007) 7-16.

C. Feng S. Mitra., Two-stage microtrap as an injection device for continuous on-line gas chromatographic monitoring., Journal of Chromatography A., 805 (1998) 169-176.

R.C. Haddon, Guest Editorial: Carbon Nanotubes, Accounts of Chemical Research, Dec. 2002, vol. 35, No. 12, p. 977.

C.H. Hussain et al., Microtrapping characteristics of single and multi-walled carbon nanotubes, Journal of Chromatography A 1185 (2008) 161-166.

M. Karwa, S. Mitra, Gas Chromatography on Self-Assembled, Single-Walled Carbon Nanotubes; Analytical Chemistry, vol. 78, No. 6, (2006) 2064-2070.

M. Kim, S. Mitra, A microfabricated microconcentrator for sensors and gas chromatography, Journal of Chromatography A, 996 (2003) 1-11.

A. Kroupa et al., Breakthrough characteristics of volatile organic compounds in the −10 to +170° C. temperature range on Tenax TA determined by microtrap technology, Journal of Chromatography A, 1038 (2004) 215-223.

S Mitra, C. Yu, Continuous gas chromatographic monitoring of low concentration sample streams using an on-line microtrap, Journal of Chromatography, 648 (1993) 415-421.

S. Mitra et al.,Characteristics of microtrap-based injection systems for continuous monitoring of volatile organic compounds by gas chromatography, Journal of Chromatography A, 727 (1996) 111-118.

S. Mitra et al., Continuous monitoring of volatile organic compounds in air emissions using an on-line membrane extraction-microtrap-gas chromatographic system, Journal of Chromatography A, 736 (1996) 165-173.

J. Pollmann et al., Evaluation of solid adsorbent materials for cryogen-free trapping—gas chromatographic analysis of atmospheric C2-C6 non-methane hydrocarbons, Journal of Chromatography A, 1134 (2006) 1-15.

Shekhar Subramoney, Novel Nanocarbons—Structure, Properties, and Potential Applications, Advanced Materials 10, No. 15, (1998) 1157-1171.

Thammakhet, et al., Microtrap modulated flame ionization detector for on-line monitoring of methane, Journal of Chromatography A, 1072 (2005) 243-248.

C.H. Wu, Studies of the equilibrium and thermodynamics of the adsorption of $Cu^{2+}$ onto as-produced and modified carbon nanotubes, Journal of Colloid and Interface Science 311 (2007) 338-346.

J. Yin et al., Magnetic surface microtraps for realizing an array of alkali atomic Bose-Einstein condensates or Bose clusters, Optics Communications 206 (2002) 99-113.

\* cited by examiner

MICROTRAP ASSEMBLY FOR GREENHOUSE GAS AND AIR POLLUTION MONITORING

CROSS-REFERENCE TO RELATED APPLICATION(S)

This application claims the benefit of U.S. Provisional Patent Application No. 61/323,864 filed Apr. 13, 2010, the entirety of which is incorporated herein by reference.

GOVERNMENT RIGHTS

The United States government may have certain rights in this invention. A portion of the work described herein was supported in part by the Department of Energy under Grant DE-FG02-07ER84894.

FIELD OF THE INVENTION

The presently disclosed subject matter relates to the adsorption of greenhouse gases and other air pollutants in microtrap preconcentrators and in particular to a microtrap assembly having sorbent including carbon nanotubes.

BACKGROUND

Global warming is a result of the increase in concentration of greenhouse gases (GHGs) in the atmosphere. GHGs selectively absorb infrared radiation and re-emit it back to the atmosphere, thereby heating the earth's surface. GHGs include carbon dioxide (76%), methane (13%), nitrous oxide (6%) and fluorocarbons (5%). Monitoring of these gases is important for the control of global warming and facilitates carbon trading strategies being implemented by the international community.

Current technologies for GHG monitoring include optical spectroscopy and gas chromatography (GC). The optical spectroscopy method includes Fourier transform infrared (FTIR) and cavity ring down (CRD) spectroscopy. These are inherently complex and expensive instruments in which quantification of multiple species with low concentration is difficult. Meanwhile, the GC analysis of some GHGs is cost-effective and provides high resolution separation for diverse components; however, the monitoring of trace levels of GHG species such as methane and chlorofluorocarbons (CFCs) remains a challenge. While the concentration of $CO_2$ is relatively high and does not require additional preconcentration, the concentration of organic species, namely methane and others such as the chlorofluorocarbon (CFCs) is of particular importance where preconcentration is necessary. Since methane is the most volatile of the GHGs, it follows that if one can preconcentrate $CH_4$, one can analyze all other greenhouse gases of interest. Similarly, other air pollutants including volatile and semivolatile organics are also of interest.

A microtrap is a capillary tubing packed with a sorbent for analyte retention, along with the capability of rapid desorption. Microtraps have been fabricated from microbore capillary as well as via silicon micromachining D. J. Butcher, Microchem. J., 66 (2000) 55. Their small dimension allows rapid desorption of adsorbed compounds, with potential advantages of faster operation, smaller bandwidth and low detection limit. Consequently, they are ideal for detectors such as photo ionization and flame ionization detectors and in conjunction with micro gas chromatography (GC). Microtraps are used for sample delivery to analytical instruments when preconcentration is required. A microtrap may serve as an integrated concentration-injection device. See, S. Mitra et al., J. Chromatogr. A 736 (1996) 165-173; A. Kroupa et al., J. Chromatogr. A 1038 (2004) 215; J. Pollmann et al., J. Chromatogr. A 1134 (2006) 1. Sorbent selection is important because the analytes need to be retained in a small quantity of sorbent for rapid, quantitative detection. J. Yin et al., Opt. Commun. 20 (2002) 99; C. H. Hussain et al., J. Chromatogr. A 1185 (2008)161.

To date, there is no commercially available preconcentrator for the greenhouse gases of interest. Accordingly, it would be advantageous to provide a microtrap for preconcentration of GHGs of interest such as methane and CFCs so that GHG monitoring of these, as well as other air pollutants, can be carried out at low concentrations.

SUMMARY OF INVENTION

In accordance with one aspect, a microtrap is provided for preconcentration of methane and CFCs so that greenhouse gas monitoring can be carried out at low concentrations. The microtrap can also be used for monitoring of organic and inorganic air pollutants. The presently disclosed subject matter employs an adsorbent that provides high specific capacity for the particular gases in question, e.g., methane, chlorofluorocarbon, etc. so that it can be effective in a microtrap. Carbon nanotubes and multiwalled carbon nanotubes (MWNTs) in particular have surprisingly been found to be an effective sorbent for preconcentration of methane and CFCs. In one aspect carbon nanotubes and particularly MWNTs are incorporated into a microtrap for use in a gas chromatography (GC) system providing an effective greenhouse gas monitor.

The microtrap assembly may be employed as a preconcentrator operable to deliver a sample to an analytical device to measure the concentrations of greenhouse gases. In accordance with one aspect a microtrap apparatus including MWNTs is provided which may be heated rapidly by an electric pulse, leading to rapid desorption of concentrated GHGs.

The microtrap assembly may include more than one capillary tube. The capillary tube may have an interior diameter of about 0.1 mm to about 5 mm. In one embodiment the microtrap may be wrapped into a coil. The length of the microtrap may be about 1 cm to about 300 cm, preferably about 1 cm to about 100 cm.

In accordance with one embodiment, the lengths of carbon nanotubes in the sorbent are from about 0.1 nm to 400 micrometers. The carbon nanotubes may be packed into the tube or form a film thickness on the capillary tube of about 0.1 to about 2000 microns. In a preferred embodiment the carbon nanotubes form a film thickness on the capillary tube of 0.1 to 100 microns.

In another embodiment, a system for detecting greenhouse gases is provided including a microtrap having a carbon nanotube sorbent operably connected to a gas inlet and a gas chromatograph. A thermal conductivity detector may be operably connected to the gas chromatograph. In one embodiment the microtrap is housed in a temperature controlled chamber. In yet a further embodiment a power source is operably connected to the microtrap for providing resistive heating thereto. A timer may be operably connected to the power source to enable an electrical pulse to the microtrap. A data acquisition device such as a computer may be operably connected to the gas chromatograph.

Microtrap apparatus in accordance with the present disclosure is effective in monitoring of GHGs, including methane and CFCs. Monitoring is possible at low levels, e.g., 0.1 ppt-10 ppm. The MWNTs show higher absorption efficiency when compared to other commercial sorbents in terms of both breakthrough time and detector response.

The breakthrough and desorption efficiency are important characteristics of a sorbent trap. For quantitative sampling, the total amount should not exceed its breakthrough volume (BTV) defined as the volume that can be sampled per unit weight of the sorbent before the analyte is lost. Based on previous reports (see, S. Mitra et al., J. Chromatogr. A 727 (1996) 111; C. Feng S. Mitra, J. Chromatogr. A 805 (1998) 169; Thammakhet, et al., J. Chromatogr. A 1072 (2005) 243), GHGs such as $CH_4$ and CFCs may be expected to have very low breakthrough volumes.

BRIEF DESCRIPTIONS OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Figure 1:
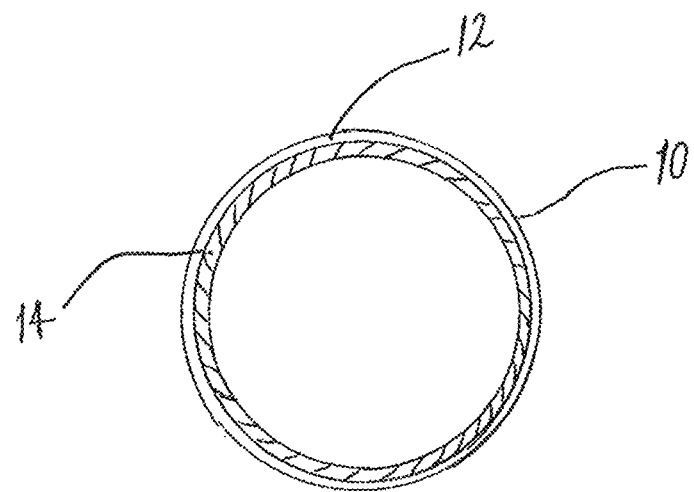
FIG. 1 is a cross-sectional view of a microtrap in accordance with one embodiment of the present disclosure.

Now referring to FIG. 1, in accordance with one embodiment a microtrap 10 includes a capillary tube 12 and carbon nanotube (CNT) sorbent 14. Carbon nanotubes have excellent mechanical strength, are thermally stable and exhibit high electrical as well as thermal conductivity. Lengths of carbon nanotubes in sorbent 14 may range from 0.1 nm to 400 micrometers while the average diameter may range from 1 to 200 nm. The carbon nanotubes may be vertically aligned. The carbon nanotubes may form a film thickness on the capillary tube of about 0.1 microns to about 2000 microns. In a preferred embodiment the carbon nanotubes form a film thickness on the capillary tube of 0.1 microns to 100 microns.

In one embodiment the sorbent includes multi-walled carbon nanotubes (MWNTs). A single-walled carbon nanotube (SWNT) is formed by rolling up a graphene layer, while multi-walled carbon nanotubes (MWNTs) consist of multiple concentric tubes. See, R. C. Haddon, Acc. Chem. Res., 2002, 35, 977-1013; S Mitra, C. Yu, J. Chromatogr. A 648 (1993) 415.

The carbon nanotube sorbent 14 can be employed in the microtrap 10 in a packed format or as a self-assembled trap. In one embodiment, the microtrap packing procedure was carried out by applying a vacuum to one of the capillary tube ends along with a vibrator to ensure uniform distribution of sorbent particles. Certain exemplary embodiments of the present invention embrace a microtrap 10 with capillary tubing 12 ranging from about 0.1 mm to about 5.0 mm interior diameter. One exemplary embodiment studied extensively experimentally was the 0.5 mm interior diameter embodiment. Microtraps of such dimensions may be wrapped into a coil of about 3 cm of diameter. The length of microtrap 10 may range from about 1 cm to about 300 cm. Preferably the microtrap has a length of about 1 cm to about 100 cm. In an exemplary embodiment the microtrap has a length of about 15 cm.

Breakthrough and desorption efficiency are important characteristics of a microtrap. Since the presently disclosed subject matter employs a design utilizing small dimensions, the microtrap 10 preferably will contain small amounts of sorbent 14, which may have a relatively low absorption capacity. For quantitative sampling, it is preferable that the sample volume not exceed its breakthrough volume, defined as the volume that can be sampled per unit weight of the sorbent before the analyte is lost.

Figure 2:
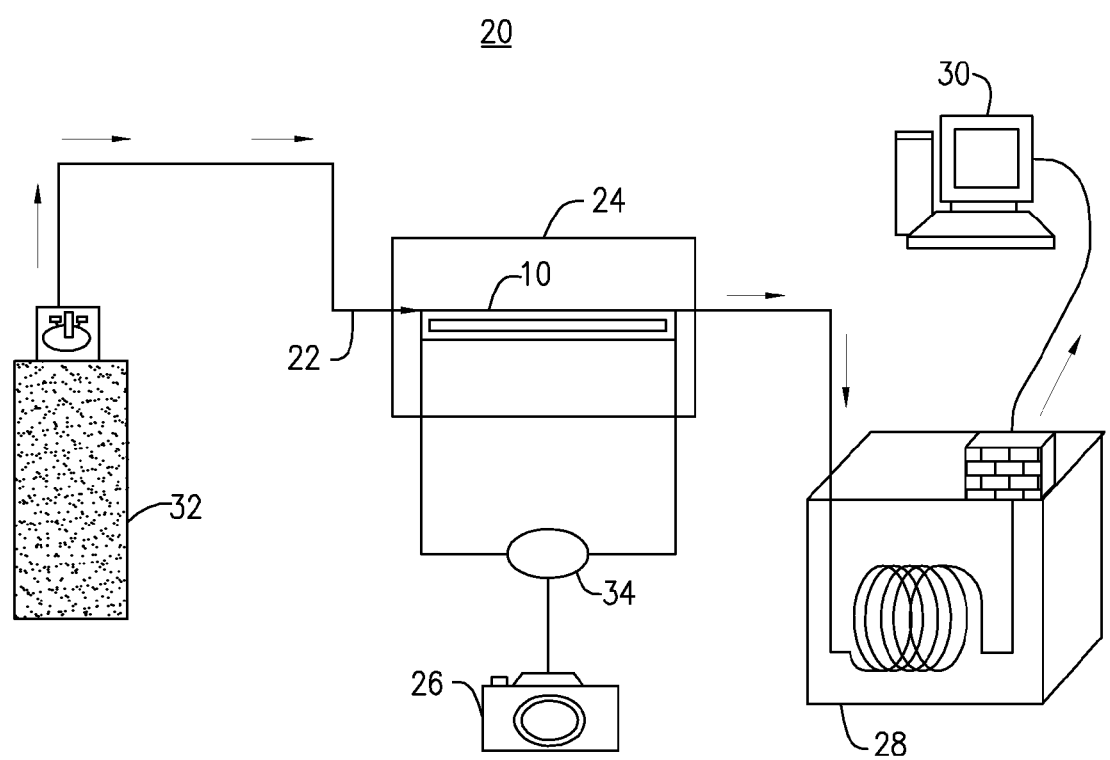
FIG. 2 is schematic diagram in accordance with one embodiment of the present disclosure.
Figure 3A:
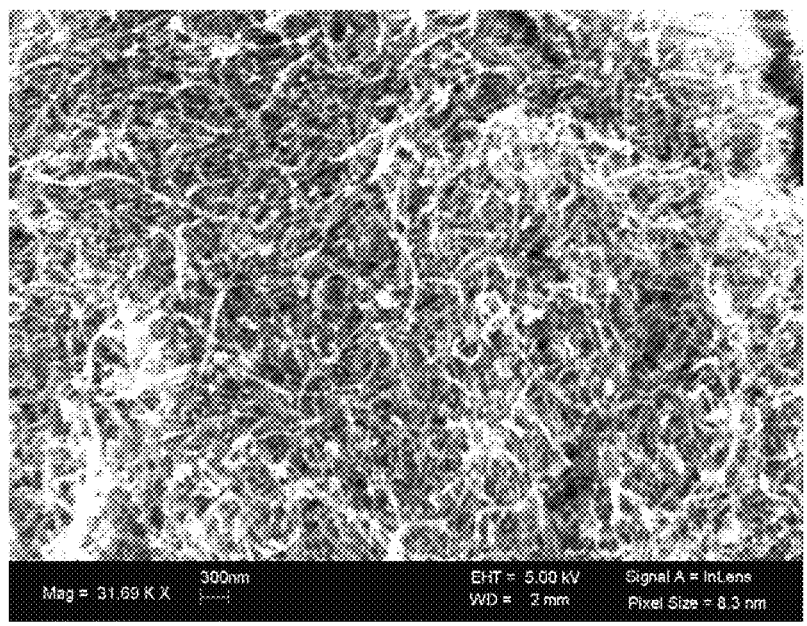
FIG. 3A is a scanning electron microscope image of the multi-walled carbon nanotubes in accordance with one embodiment of the present disclosure.
Figure 3B:
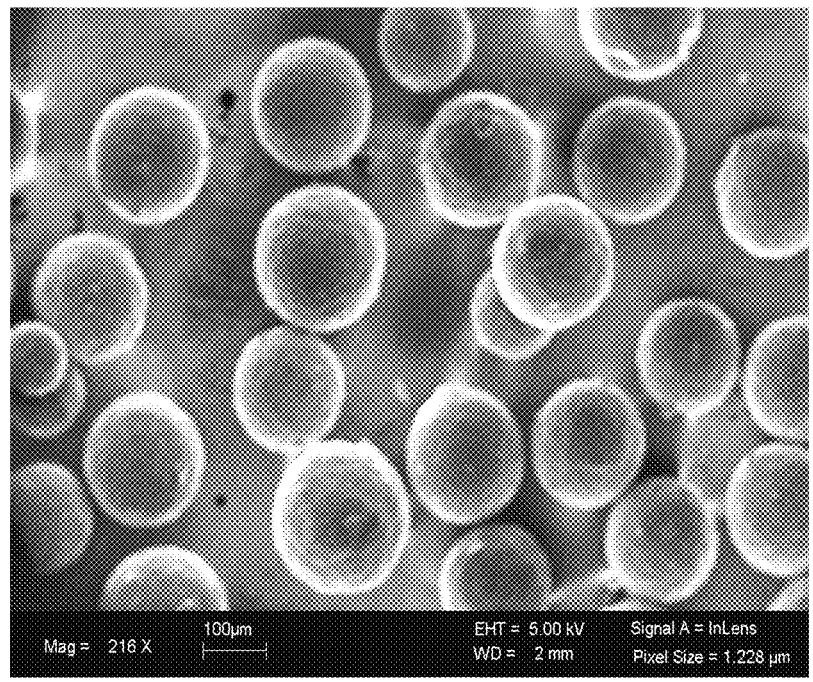
FIG. 3B is a scanning electron microscope image of a carbosieve.
Figure 3C:
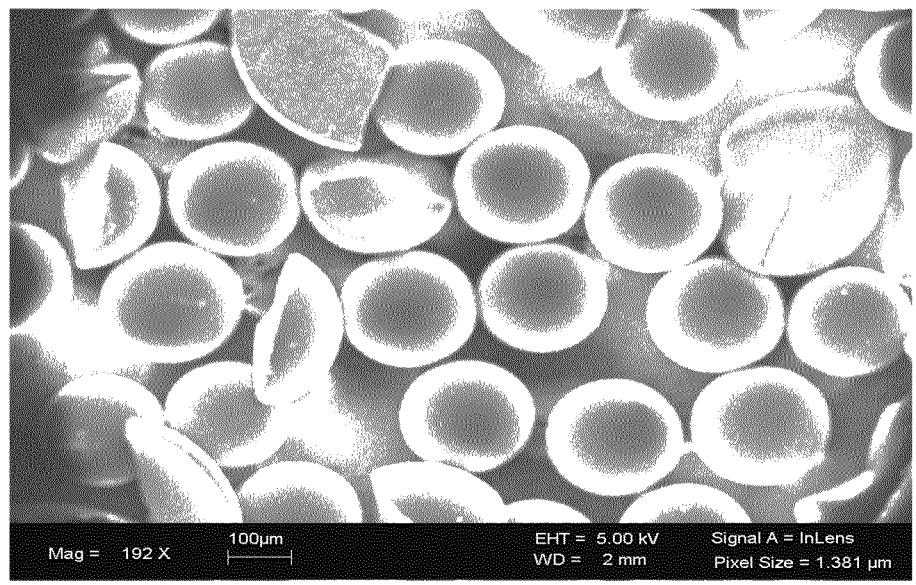
FIG. 3C is a scanning electron microscope image of a carboxene.
Figure 3D:
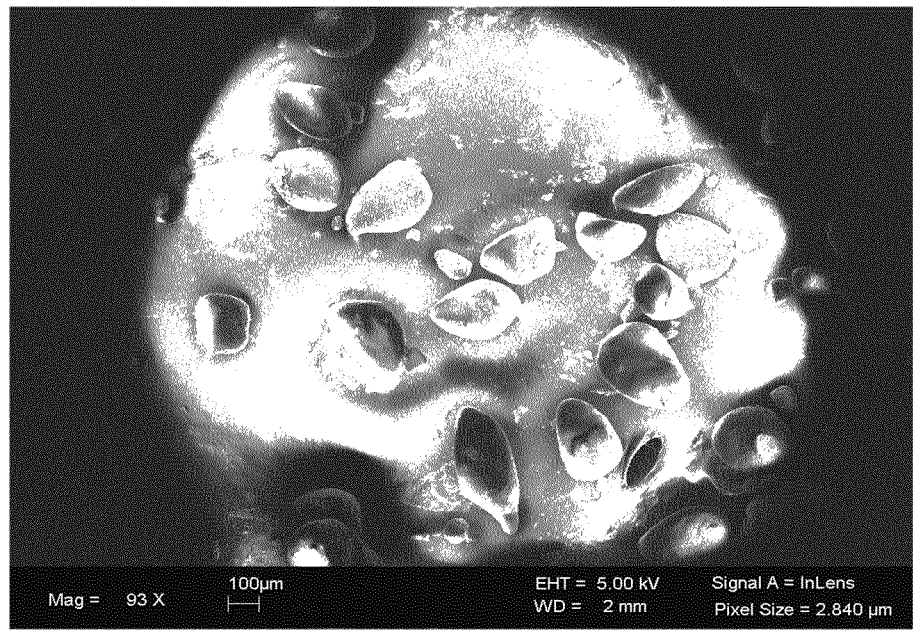
FIG. 3D is a scanning electron microscope image of a carbopack.

Now referring to FIG. 2, a system 20 employing microtrap 10 includes gas inlet 22, microtrap 10, temperature controlled chamber 24, timer 26, thermal conductivity detector (TCD) equipped gas chromatograph 28 for analysis and data acquisition device 30 such as a computer. A gas dispensing unit 32 may be connected to inlet 22. The microtrap 10 may be resistively heated using pulses of electric current from a power supply 34. Microtrap 10 serves as a preconcentrator of greenhouse gases so that low levels of greenhouse gases may be detected and analyzed in the gas chromatograph 28 and data acquisition device 30.

Experiments

The experimental examples herein are set forth so as to provide those of ordinary skill in the art with a complete disclosure and description of how to make and use the present invention, and are not intended to limit the scope of what the inventors regard as their invention nor are they intended to represent that the experiments below are all or the only experiments performed.

To test an embodiment employing a 0.5 mm microtrap, an experimental system was used similar to the one shown in FIG. 2. A gas standard containing approximately 10 ppm of $CH_4$ was purchased. It flowed into the microtrap 10 of system 20 continuously while the $CH_4$ was trapped by the sorbents.

Microtrap 10 was resistively heated with about a 7-about 10 ampere pulse of electric current from power supply 34.

Desorption was applied at regular intervals, so that the trapped organics were desorbed and detected by the gas chromatograph with the thermal conductivity detector 28. The duration of the pulse was between about 0.5 to about 2.5 seconds. An electric timer 26 was used to control the durations and interval between electrical pulses. A power resistor was put in series to control the current. Gas chromatograph with TCD 28 was used for analysis using a capillary column. The microtrap 10 was packed with about 13 mg of four different adsorbents in a silcosteel tubing approximately 15 cm long. The adsorbents used for this experiment were Multiwall Carbon Nanotubes from Cheap Tubes, USA, carbosieve, carboxene and carbopack from Sigma-Aldrich, USA.

Conventional carbon-based sorbents may be sub-classified into activated carbon, carbon molecular sieves and graphitized carbon blacks. Activated carbons are micro-porous materials with a wide distribution of pore size and high specific surface areas. The carbon forms micro-crystallites with a graphitic structure. The carbon in graphitized carbon blacks is organized in a hexagonal graphite lattice forming planar layers. The higher the degree of graphitization, the lower the specific surface area. The carbon molecular sieves are synthesized by thermal decomposition of polymers such as poly (vinylidene chloride), and poly vinyl chloride. They are micro-porous sorbents with a sharp pore size distribution and high specific surface areas.

Now referring to FIGS. 3A-3D, scanning electron microscopic images of the sorbents used in this experiment are shown. It is evident that the morphology of the CNTs, in this example, MWNTs, is quite different from the other sorbents tested. Carboxene, carbopack and carbosieve are porous sorbents with significant internal surface areas. The CNTs themselves are nonporous structures. This is one of the major advantages of CNTs, where the solute is held on the surface by van der Walls type forces, thus eliminating the mass transfer resistance related to the diffusion into elaborate pore structures. The high capacity of the CNTs comes from their large aspect ratio.

Figure 4:
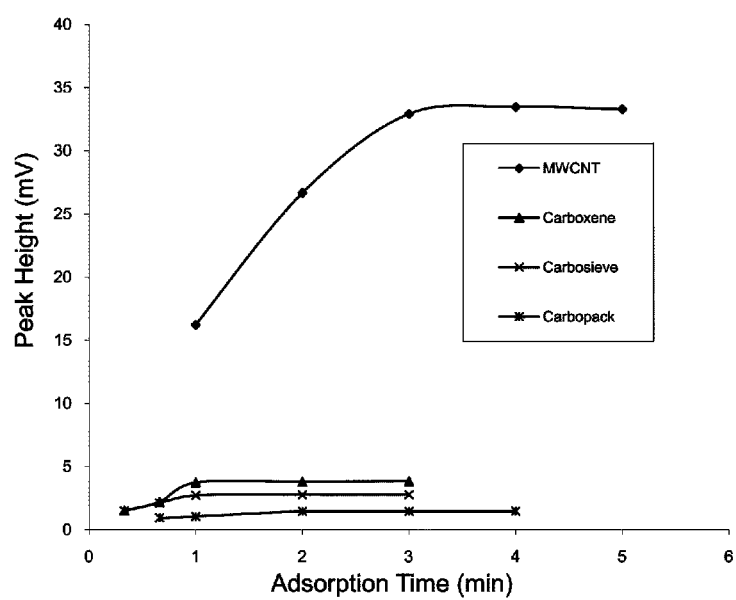
FIG. 4 is a graphical depiction showing the detector response for different sorbents at different injection intervals at room temperature for methane in accordance with one embodiment of the present disclosure.

The sorption capacity of the microtrap 10 was evaluated by studying the breakthrough time which is defined as the time required by an analyte eluting through. To compare the sorption capacity of the different sorbents used, the breakthrough times of said sorbents (MWNT, carboxene, carbosieve and carbopack) were estimated, and are presented in FIGS. 4 and 5 and Table 1. FIG. 4 is a plot of detector response as a function of absorption time (measured as the interval between injections). The time required to reach the maximum point is the measure of breakthrough time.

TABLE 1

Breakthrough Characteristics and Enthalpy Calculation of various adsorbents

| | Adsorbents | | | |
|---|---|---|---|---|
| | MWNT | Carboxene | Carbosieve | Carbopack |
| Type of Adsorbent | Nano tube | Carbon molecular sieve | Carbon molecular sieve | Graphitized carbon black |
| Surface Area | >110 m²/g | 500 m2/g | 820 m²/g | 10 m²/g |
| Temperature | | Breakthrough Characteristics | | |
| 20 | 3 | 1 | 1 | 1 |
| 10 | 4 | 3 | 3 | 2 |
| 0 | 5 | 3 | 4 | 2 |

TABLE 1-continued

Breakthrough Characteristics and Enthalpy Calculation of various adsorbents

| | Adsorbents | | | |
|---|---|---|---|---|
| | MWNT | Carboxene | Carbosieve | Carbopack |
| −10 | 7 | 3.5 | 4 | 3 |
| −20 | 8 | 4 | 4 | 4 |
| Enthalpy of adsorption (KJ/mol) | 5.1 | 2.3 | 1.7 | 1.5 |

Figure 5:
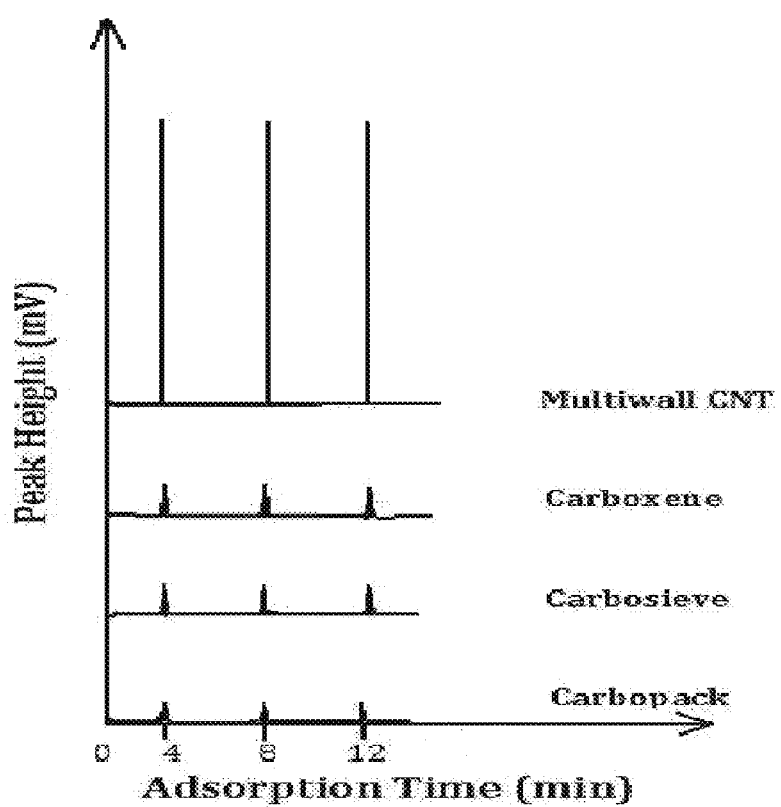
FIG. 5 is a graphical depiction showing the relative detector responses using the various adsorbents in accordance with one embodiment of the present disclosure.

The MWNT showed the longest breakthrough time (FIG. 4). The stronger sorption also allowed more greenhouse gas to be trapped in the microtrap 10, as a result the response in terms of peak height was much higher from MWNT than from the other sorbents (FIG. 5). According to preliminary estimates, using a MWNT microtrap, detection sensitivity of the analyzer in which the microtrap is employed will be increased by two to three orders of magnitude and would allow for detection of GHG in the ppb range.

Breakthrough Characteristics as a Function of Temperature

Figure 6:
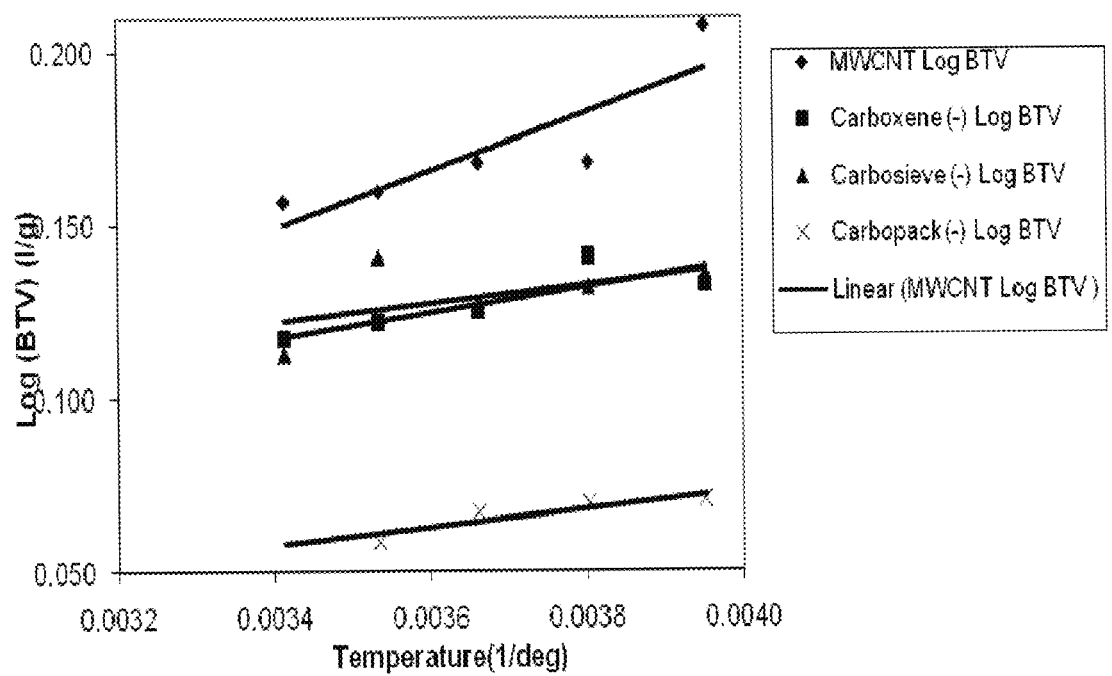
FIG. 6 is a graphical depiction showing the breakthrough volume as a function of temperature for various sorbents and at different temperature in accordance with one embodiment of the present disclosure.

One way to enhance sensitivity and increase the breakthrough time is lowering the temperature of a microtrap. When the sorption temperature is decreased, the breakthrough time increased. The breakthrough time of one embodiment of the present invention more than doubled as the temperature was lowered from 20° C. to −20° C. The results followed the Van't Hoff-type relationship as shown in FIG. 6. The plot of Log BTV as a function of 1/t and was found to be linear according to: Log(BTV)=$k_1$ 1/t+$k_2$, where BTV is the breakthrough volume (the volume that can be sampled per unit weight of the sorbent before the analyte breaks through the sorbent bed) and $k_1$ and $k_2$ are constants. It was interesting to note that the slopes varied for the different sorbents utilized with MWNT showing the highest while carbopack the lowest.

The isoteric heat of adsorption, $\Delta H_s$ is the amount of heat released when an atom adsorbs on a substrate, and is related to the activation energy of sorption for a sorbate-sorbent system. The strength of interaction of compound with the surface of the of the adsorbent is represented by the enthalpy of adsorption, $\Delta H_s$, given by $$\Delta H_s = -R \frac{\partial (\ln Vg)}{\partial (1/T)}$$

The $\Delta H_s$ were obtained from the slope of plots of ln Vg vs 1/T, where Vg is the retention volume of the organic compound on the sorbent. A linear dependence indicated a constant value of the isoteric heat of adsorption in the temperature range studied, while relative change in $\Delta H_s$ of sorbents with temperature is attributable with the activation of the sorbent surface. See, E. Diaz, S. Ordonez, A. Vega, J. Colloid Interface Sci. 305 (2007) 7; M. Karwa, S. Mitra, Anal Chem. 78 (2006) 2064-2070; C. H. Wu, J. Colloid Interface Sci. 311 (2007) 338. These values for greenhouse gases are presented in Table 2. The maximum $\Delta H_s$ was for MWNT, suggesting that it had the strongest interaction with the analyte. This was followed by carboxene, carbosieve and carbopack. Once again this demonstrated that the mechanisms of adsorption were quite similar in these other sorbents.

TABLE 2

Breakthrough Characteristics of GHGs Under Room Temperature

| Samples | | Methane (CH$_4$) | | Chlorofluorocarbons (CFCs) | |
| --- | --- | --- | --- | --- | --- |
| Adsorbents | Surface Area (m$^2$/g) | Breakthrough Time (mins) | Detector Response (mV) | Breakthrough Time (mins) | Detector Response (mV) |
| MWNT - pure | 150-300 | 3 | 19.208 | 9 | 714.55 |
| Carboxene | 500 | 2 | 2.803 | 9 | 24.33 |
| Carbopack | 10 | 1 | 1.490 | 4 | 19.22 |

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

What is claimed is:

1. A system for detecting greenhouse gases comprising a microtrap assembly comprising at least one capillary tube comprising sorbent comprising carbon nanotubes and a temperature controlled chamber housing the microtrap assembly wherein the temperature controlled chamber is operable to lower a temperature of the microtrap assembly below ambient temperature.

2. The system according to claim 1 wherein the carbon nanotubes comprise multiwalled carbon nanotubes.

3. The system according to claim 1 wherein the sorbent consists of carbon nanotubes.

4. The system according to claim 1 wherein the sorbent consists of multiwalled carbon nanotubes.

5. The system according to claim 1 wherein the microtrap assembly comprises plural capillary tubes.

6. The system according to claim 1 consisting of a single capillary tube.

7. The system according to claim 1 wherein the capillary tube has an interior diameter of about 0.1 mm to about 5.0 mm.

8. The system according to claim 1 wherein the capillary tube has an interior diameter of 0.5 mm.

9. The system according to claim 1 wherein the microtrap is wrapped into a coil.

10. The system according to claim 1 wherein the microtrap has a length of about 1 cm to about 300 cm.

11. The system according to claim 1 wherein the microtrap has a length of about 1 cm to about 100 cm.

12. The system according to claim 1 wherein the microtrap has a length of about 15 cm.

13. The system according to claim 1 wherein the lengths of carbon nanotubes in the sorbent are from about 0.1 nm to about 400 micrometers.

14. The system according to claim 1 wherein the carbon nanotubes form a film thickness on the capillary tube of about 0.1 microns to about 2000 microns.

15. The system according to claim 1 wherein the carbon nanotubes form a film thickness on the capillary tube of about 0.1 microns to about 100 microns.

16. The system according to claim 1 further comprising a gas inlet and a detector or a gas chromatograph, wherein the microtrap assembly is operably connected to the gas inlet and the detector or gas chromatograph.

17. The system according to claim 16 further comprising a detector operably connected to a gas chromatograph.

18. The system according to claim 16 further comprising a power source operably connected to the microtrap assembly for providing resistive heating to the microtrap assembly and a timer operably connected to the power source to enable an electrical pulse to the microtrap assembly.

19. The system according to claim 16 further comprising a data acquisition device operably connected to a gas chromatograph.

20. The system according to claim 1 operably connected to a gas inlet and a detector, sensor or a gas chromatograph, wherein the system is operable to detect organic and inorganic air pollutants.

21. The system according to claim 20, wherein the pollutant is a volatile organic compound.

22. The system according to claim 1 wherein the temperature controlled chamber is operable to cool the microtrap assembly below 20° C.

23. The system according to claim 1 wherein the temperature controlled chamber is operable to cool the microtrap assembly to at least −20° C.

* * * * *